United States Patent [19]
Suwa et al.

[11] Patent Number: 5,939,309
[45] Date of Patent: *Aug. 17, 1999

[54] BIFIDOBACTERIUM BIFIDUM PROLIFERATION PROMOTING COMPOSITION CONTAINING XYLOOLIGOSACCHARIDE

[75] Inventors: Yoshihide Suwa; Kunimasa Koga; Shigeaki Fujikawa; Masako Okazaki, all of Osaka; Toshio Irie, Aichi-ken; Toshiyuki Nakada, Osaka, all of Japan

[73] Assignee: Suntory Limited, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/826,531

[22] Filed: Apr. 2, 1997

Related U.S. Application Data

[63] Continuation of application No. 08/625,113, Apr. 1, 1996, abandoned, which is a continuation of application No. 08/454,002, May 30, 1995, abandoned, which is a continuation of application No. 08/363,589, Dec. 23, 1994, abandoned, which is a continuation of application No. 08/236,245, May 2, 1994, abandoned, which is a continuation of application No. 08/110,675, Aug. 9, 1993, abandoned, which is a continuation of application No. 07/968,462, Oct. 29, 1992, abandoned, which is a continuation of application No. 07/717,176, Jun. 18, 1991, abandoned, which is a continuation of application No. 07/114,991, Oct. 30, 1987, abandoned.

[30] Foreign Application Priority Data

Oct. 30, 1986 [JP] Japan ................................. 61-258757

[51] Int. Cl.$^6$ .................................................. C12N 5/00
[52] U.S. Cl. .................................. 435/253.1; 435/252.1; 435/252.9; 435/253.6; 435/244; 426/61; 426/71; 514/25; 514/54
[58] Field of Search ............................. 435/253.1, 252.1, 435/252.9, 253.6, 244; 426/61, 71; 514/25, 54

[56] References Cited

FOREIGN PATENT DOCUMENTS 0242592   10/1986   Japan ..................................... 435/100

OTHER PUBLICATIONS

Shokuhin Kogyo (The Food Industry), vol. 30, No. 16 (Aug. 1987), pp. 31–39 (partial English translation), with Verified Translation Affidavit by Tadahiko Kurita.
European Search Report, Application No. EP 87 11 5999.
Chemical Abstract No. 60–114186 (Japan), Jun. 6, 1985.
Data Cab Abstract No. 78404633, "Fermentation of mucins and plant polysaccharides by anaerobic bacteria from the human colon", vol. 34, No. 5, (1977), pp. 529–533.
Chemical Abstract No. 49953b, "Fermentation of glucose, lactose, galactose, mannitol, and xylose by bifidobacteria", vol. 2, (1968), pp. 472–478.
Patent Abstract No. 61–285999, Japan, Dec. 16, 1983.
Patent Abstract No. 58–201980 (Japan), vol. 8, No. 41, Nov. 25, 1983.
Patent Abstract No. 57–18982 (Japan), Jan. 30, 1982.
Bergey's Manual of Systematic Bacteriology, vol. 2, 1956, p. 1217.
Bergey's Manual of Systematic Bacteriology vol. 2 1986 p. 1217.

*Primary Examiner*—Leon B. Lankford, Jr.
*Attorney, Agent, or Firm*—Pillsbury Madison & Sutro LLP

[57] ABSTRACT

A *Bifidobacterium bifidum* proliferation promoting composition comprising a xylooligosaccharide which contains xylobiose as its principal component is disclosed. The xylooligosaccharide is obtained by enzymatically or physicochemically treating either xylan or hemicellulose derived from a natural source. *Bifidobacterium bifidum* which is useful for man is encouraged to proliferate in the intestines by the xylooligosaccharide which is not readily assimilated by *Escherichia coli* but is readily utilized by *Bifidobacterium bifidum*. The xylooligosaccharide is advantageously stable when exposed to acids or heat.

6 Claims, 9 Drawing Sheets

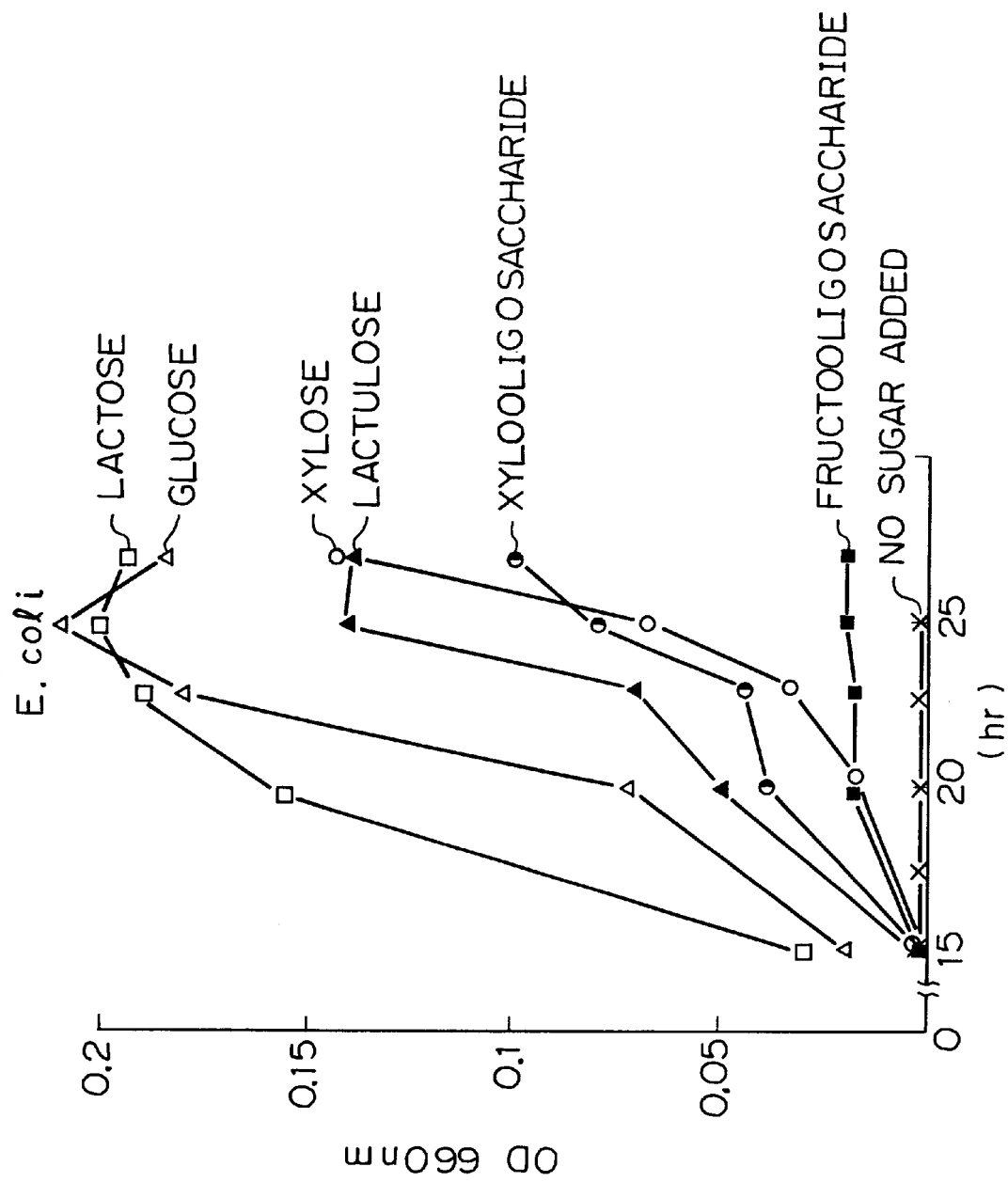
Fig. 2-A

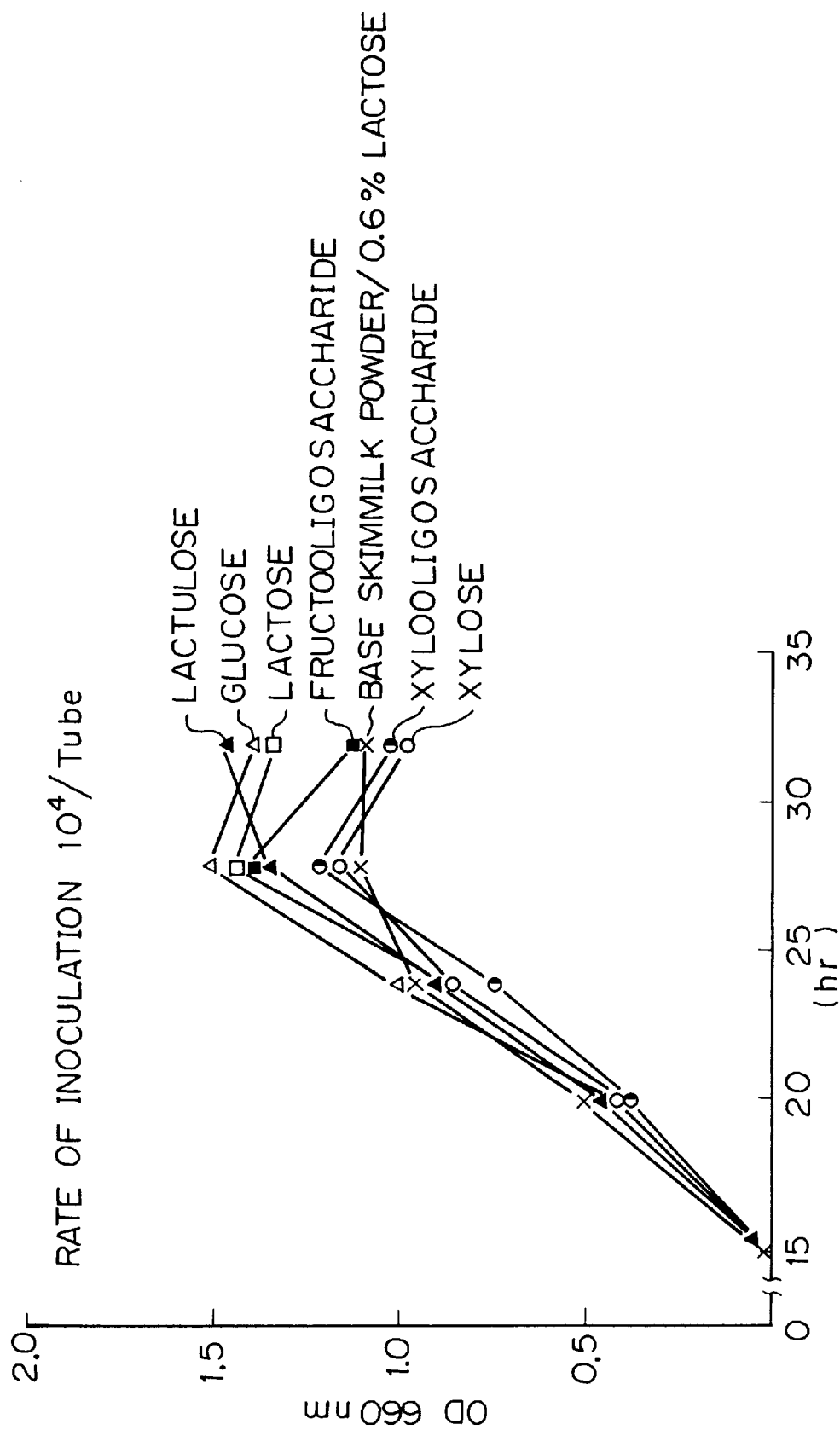

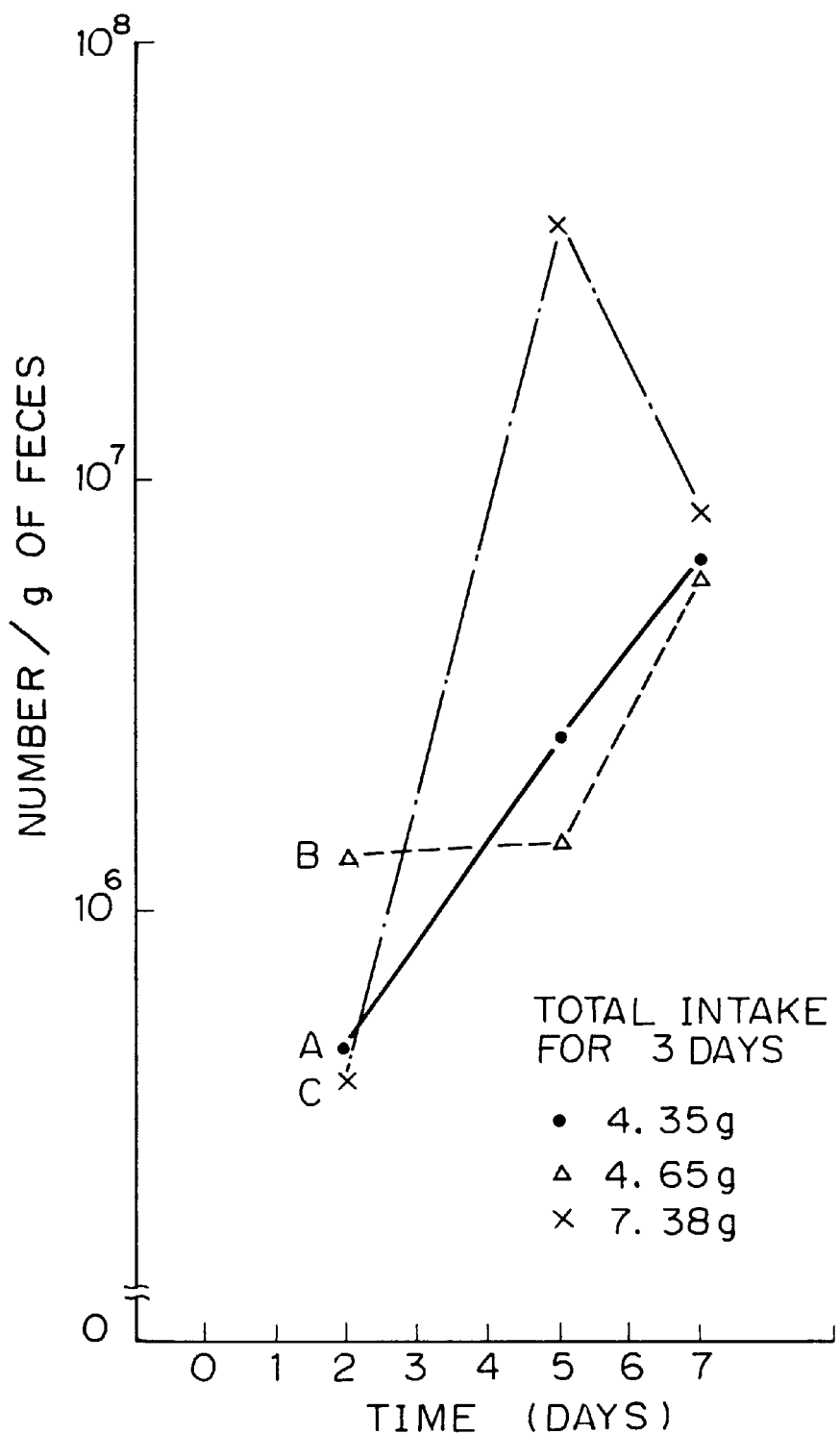

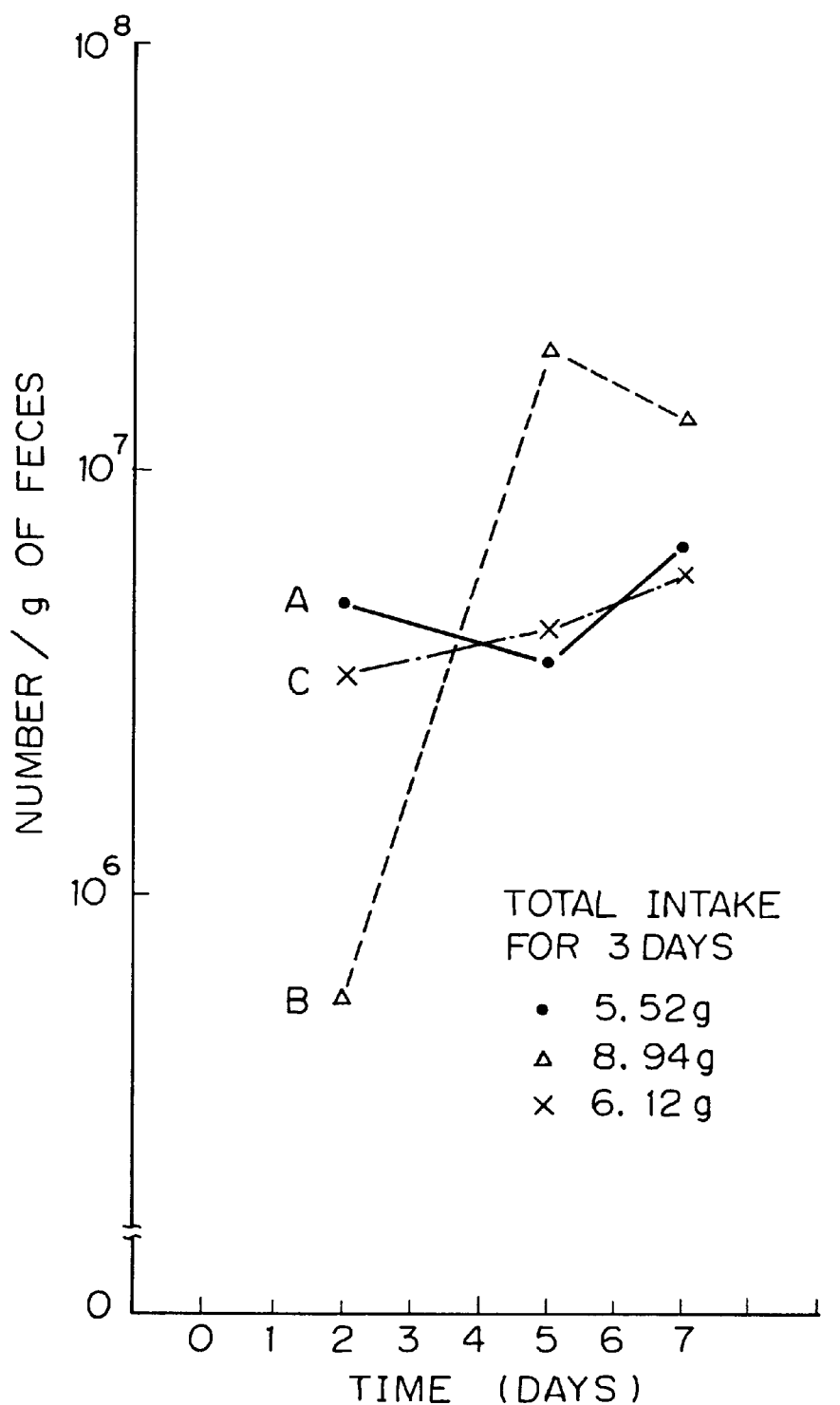
Fig. 3-B
GROUP OF RATS TO WHICH FRUCTOOLIGOSACCHARIDE WAS ADMINISTERED

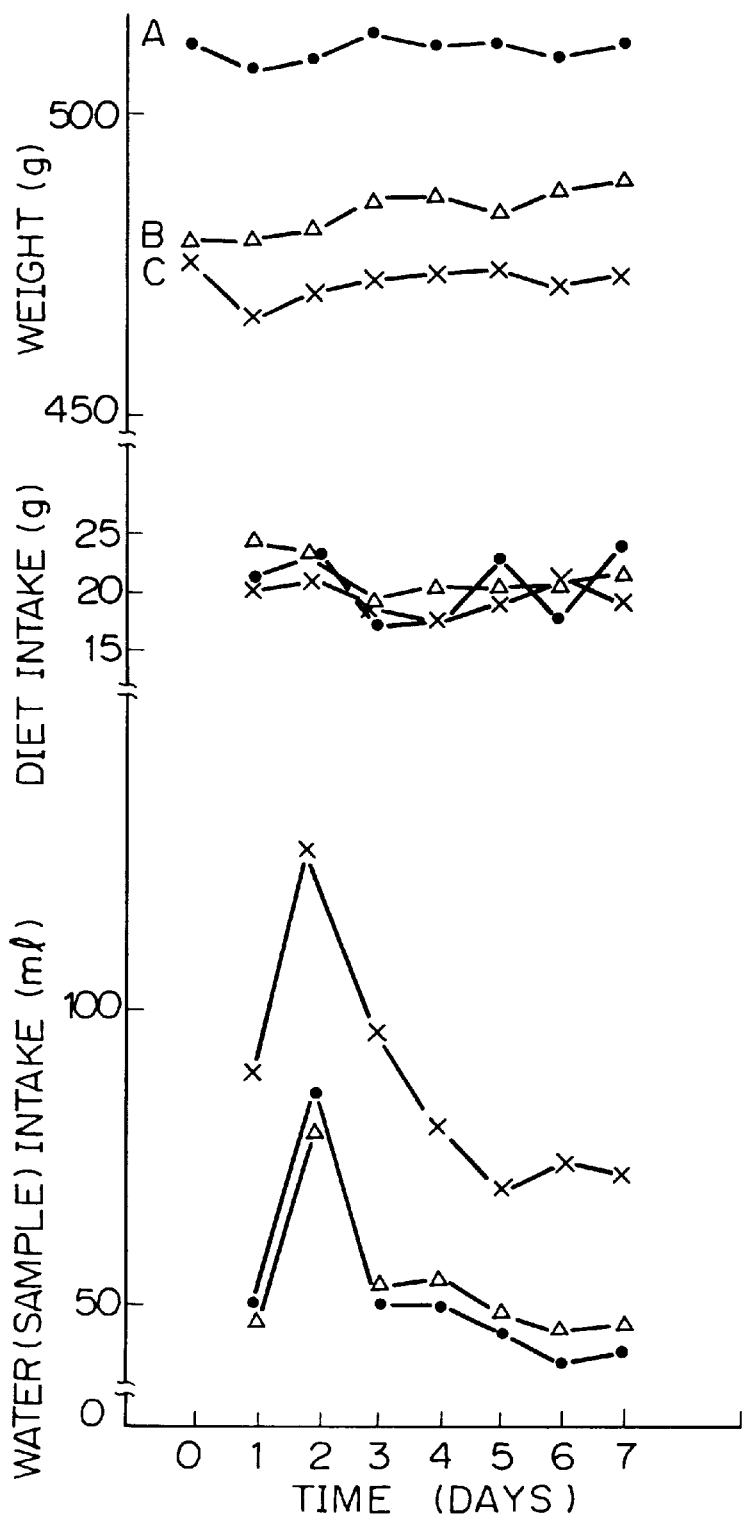
Fig. 4-A
GROUP OF RATS TO WHICH XYLOOLIGOSACCHARIDE WAS ADMINISTERED

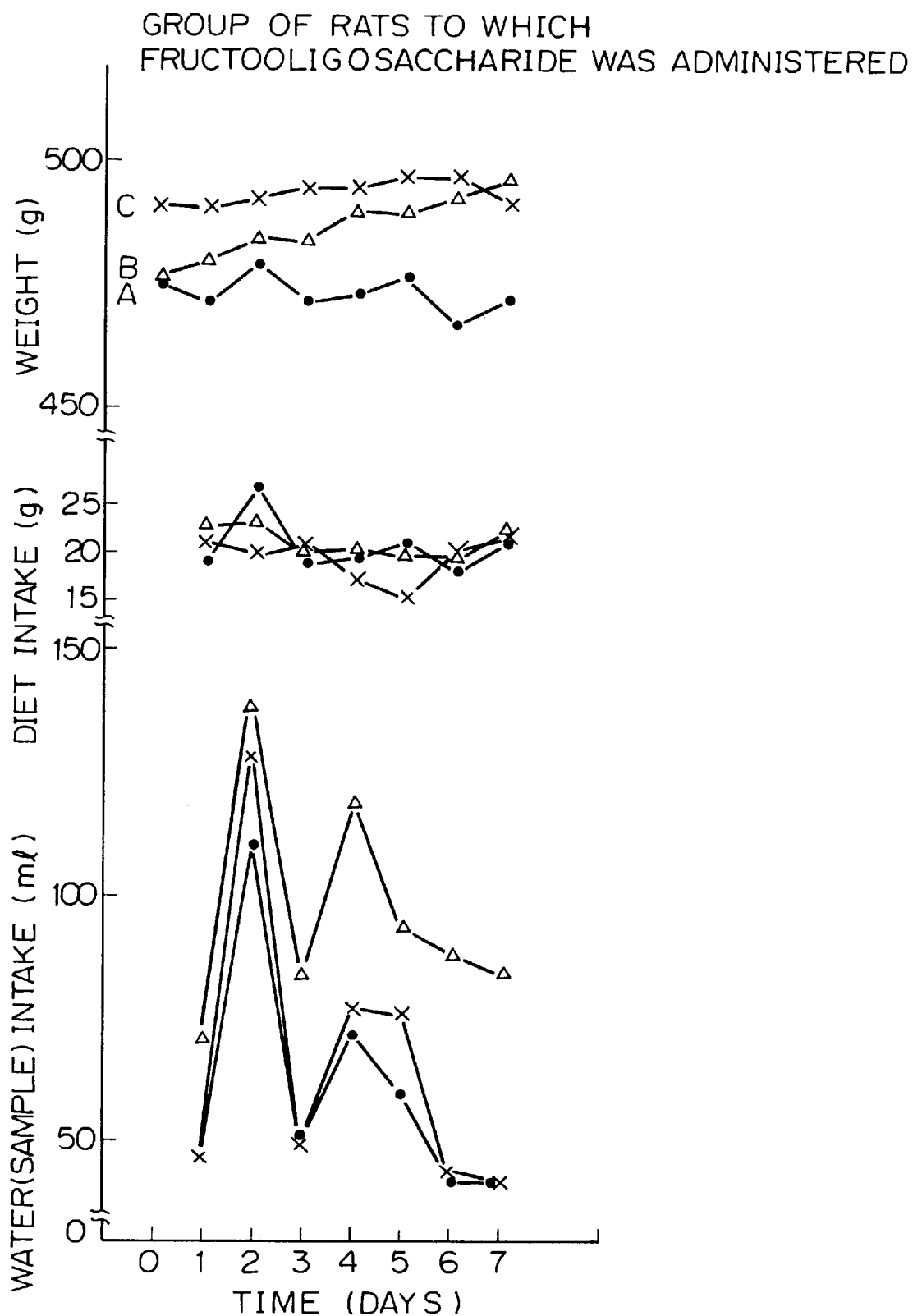
Fig. 4-B

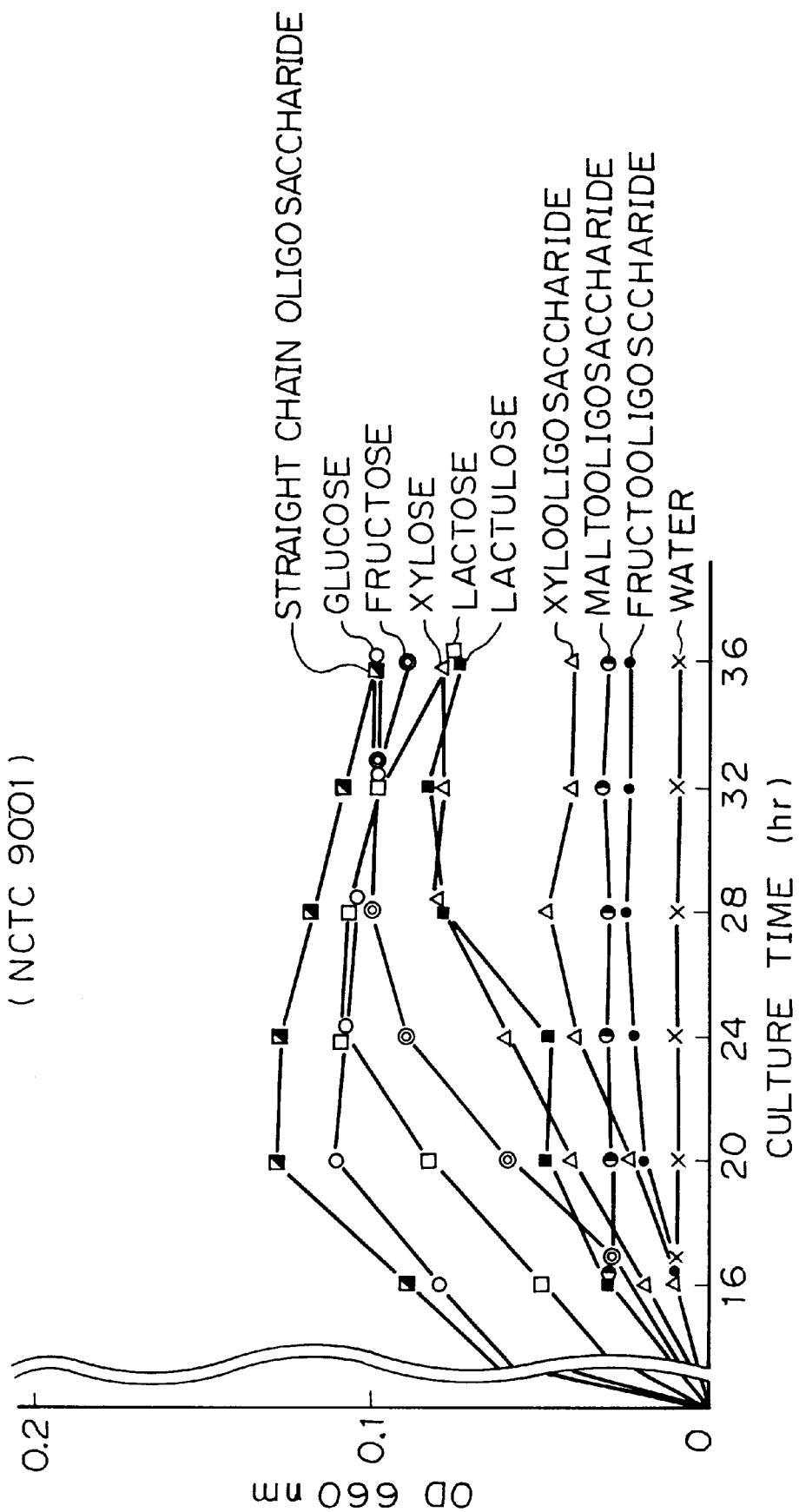

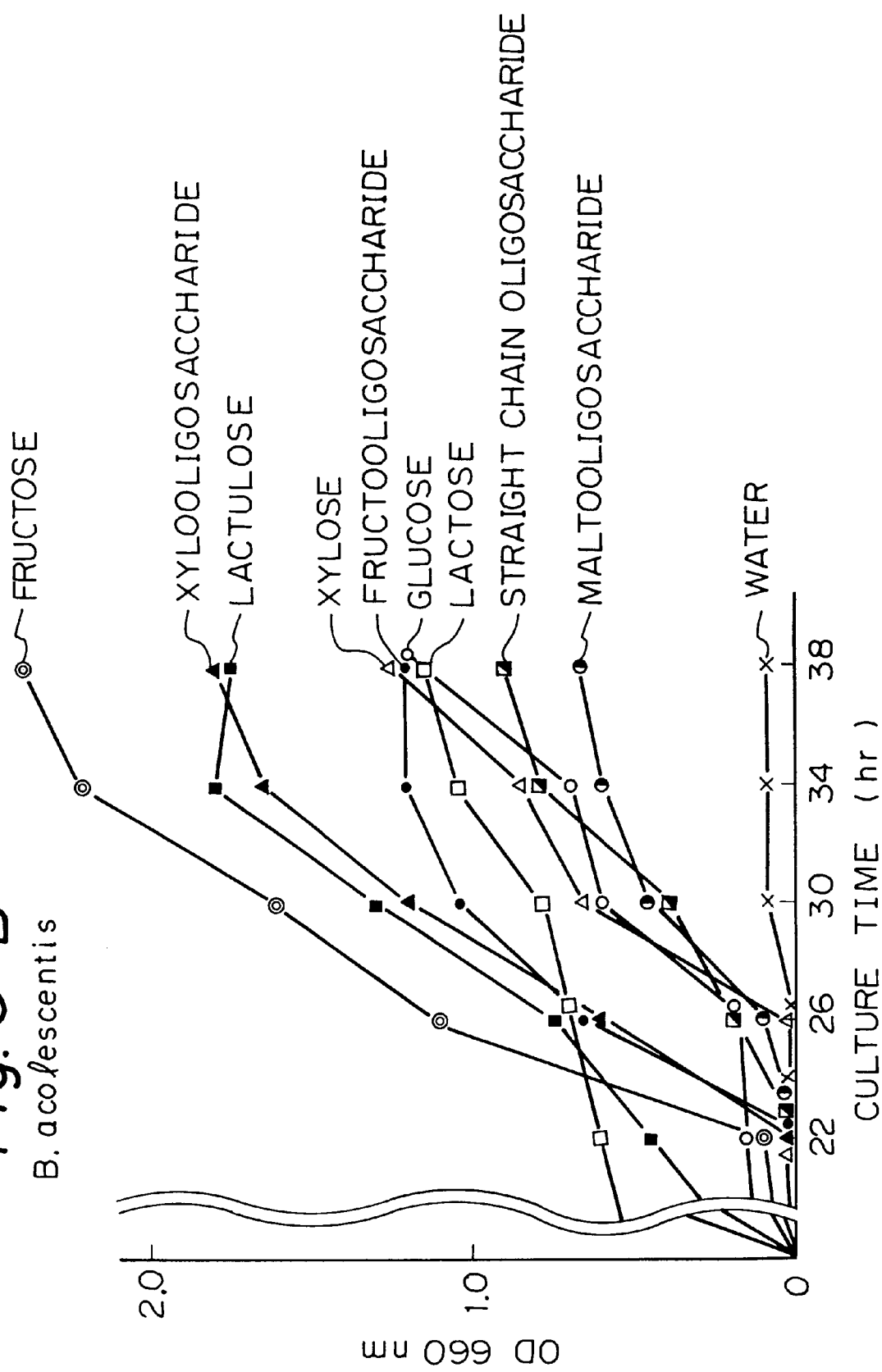

BIFIDOBACTERIUM BIFIDUM PROLIFERATION PROMOTING COMPOSITION CONTAINING XYLOOLIGOSACCHARIDE

This is a continuation of appln. Ser. No. 08/625,113, filed on Apr. 1, 1996, which is abandoned upon the filing hereof; which is a continuation of appln. Ser. No. 08/454,002, filed on May 30, 1995 now abn.; which is a continuation of appln. Ser. No. 08/363,589, filed on Dec. 23, 1994 now abn., which is a continuation of appln. Ser. No. 08/236,245 filed May 2, 1994 now abn., which is a continuation of appln. Ser. No. 08/110,675, filed on Aug. 9, 1993 now abn., which is a continuation of appln. Ser. No. 07/968,462, filed on Oct. 29, 1992 now abn., which is a continuation of appln. Ser. No. 07/717,176 filed Jun. 18, 1991, now abn., which is a continuation of appln. Ser. No. 07/114,991 filed Oct. 30, 1987 now abn.

BACKGROUND OF THE INVENTION

The present invention relates to a *Bifidobacterium bifidum* proliferation promoting composition. More particularly, the present invention pertains to a *Bifidobacterium bifidum* proliferation promoting composition comprising a xylooligosaccharide which contains xylobiose as its principal component.

Among a large number of known bacteria that constitute the enterobacterial flora, *Bifidobacterium bifidum* is one of the bacteria which are regarded as useful to man. Numerous reports have been made on the physiological significance of *Bifidobacterium bifidum*. It is widely known that *Bifidobacterium bifidum* has the following favorable activities: e.g., the activity of suppressing putrefaction caused by entero putrefactive bacteria; the activity of preventing production of toxic amines; the activity of suppressing the proliferation of pathogenic bacteria by the production of organic acids such as lactic acid, acetic acid, etc.; and the activity of promoting digestion and absorption of nutrients.

It is known that the maintenance of a balance between the various bacteria that constitute the enterobacterial flora is closely related to man's health and, when pathogenic bacteria which are usually in the minority in the intestines become predominant, the symptoms of a disease develop. A typical example is diarrhea which occurs as a result of the disappearance of *Bifidobacterium bifidum* or the action of *Escherichia coli* or Staphylococcus. *Bifidobacterium bifidum* is also closely related to infant health. More specifically, *Bifidobacterium bifidum* is predominant in the enterobacterial flora of healthy infants, but in the case of an infant suffering from exudative diathesis, certain kinds of enterococcus which suppress proliferation of *Bifidobacterium bifidum* are at all times predominant in the enterobacterial flora. It is known that the feces of a dysenteric infant have a markedly lowered *Bifidobacterium bifidum* content and the relative proportions of the various bacteria in the enterobacterial flora is considerably out of balance.

On the basis of these various known facts, a typical well-balanced enterobacterial flora is now considered to be such that *Bifidobacterium bifidum*, which has excellent staying and proliferation potencies in the intestines, is most predominant at all times.

In view of the useful activities of *Bifidobacterium bifidum*, various kinds of *Bifidobacterium bifidum*-containing preparations and dairy products have recently been developed for the purpose of increasing the amount of *Bifidobacterium bifidum* in the intestines.

However, if *Bifidobacterium bifidum* is taken orally, it will not generally stay in the intestines, and in many cases, as soon as the intake of *Bifidobacterium bifidum* is stopped, the enterobacterial flora returns to the previous state.

It is considered that the most essential factor for the proliferation of *Bifidobacterium bifidum* in the intestines is saccharides, and the effectiveness of lactulose for this purpose was in the past pointed out.

Lactulose is a sugar which is obtained by replacing the glucose portion of lactose with fructose and which can be slightly assimilated. Therefore, when lactulose is taken orally, most of it reaches the large intestine without being absorbed into the body and is assimilated by enterobacteria. However, lactulose is not necessarily assimilated preferentially by *Bifidobacterium bifidum* as it is also assimilated by other enterobacteria such as *Escherichia coli,* Clostridium, etc. It is therefore difficult to selectively encourage *Bifidobacterium bifidum* alone to proliferate.

Recently, studies have been vigorously under taken to develop a method of promoting the proliferation of *Bifidobacterium bifidum* by means of saccharides, and it has been found that fructooligosaccharide, isomaltose, etc. are effective in promoting the proliferation of *Bifidobacterium bifidum*. However, in the case of isomaltulose, although its *Bifidobacterium bifidum* proliferation activity is found in vitro, the activity disappears in vivo. Therefore, isomaltose is less effective as a *Bifidobacterium bifidum* proliferating saccharide.

Fructooligosaccharide is a sugar which consists of sucrose and 1 to 4 molecules of fructose which are connected thereto; it is selectively assimilated by *Bifidobacterium bifidum* and neither digested nor absorbed by a living body. Accordingly, it has been confirmed that fructooligosaccharide can be used to promote selectively the proliferation of *Bifidobacterium bifidum* in the intestines. However, fructooligosaccharide is prepared by transferring fructose to sucrose by means of fructose transferase and the stability of the thus prepared fructooligosaccharide is not necessarily satisfactory. In particular, when it is stored for a long time in a liquid state, the sugar changes into glucose, fructose and sucrose and its *Bifidobacterium bifidum* proliferation activity lowers as it changes.

SUMMARY OF THE INVENTION

The present inventors therefore undertook exhaustive studies in order to find a saccharide which is capable of selectively encouraging *Bifidobacterium bifidum* to proliferate in the intestines and, as a result, have found in vitro that xylooligosaccharide is not readily assimilated by *Escherichia coli* but is readily utilized by *Bifidobacterium bifidum*. The present inventors have found in vivo also that if xylooligosaccharide is taken orally, the proliferation of *Bifidobacterium bifidum* in the intestines is promoted. The present invention has been accomplished on the basis of these findings.

BRIEF DESCRIPTION OF THE DRAWINGS

FIG. 2-A shows proliferation profiles in vitro of *Escherichia coli* in various culture media;

FIG. 2-B shows proliferation profiles in vitro of *Bifidobacterium bifidum* (*Bifidobacterium longum*);

FIG. 3 shows changes in the number of individuals of *Bifidobacterium longum* per gram of the feces of a group of rats to which xylooligosaccharide was administered and those of a group of rats to which fructooligosaccharide was administered;

FIG. 4 shows changes in the weight, diet intake and water intake of a group of rats to which xylooligosaccharide was administered and a group of rats to which fructooligosaccharide was administered;

FIG. 5-A shows proliferation profiles of a strain of *Escherichia coli* which is different from that employed in the case of FIG. 2-A; and FIG. 5-B shows proliferation profiles of *Bifidobacterium bifidum* (*Bifidobacterium adolescentis*).

DETAILED DESCRIPTION OF THE INVENTION

Figure 1:
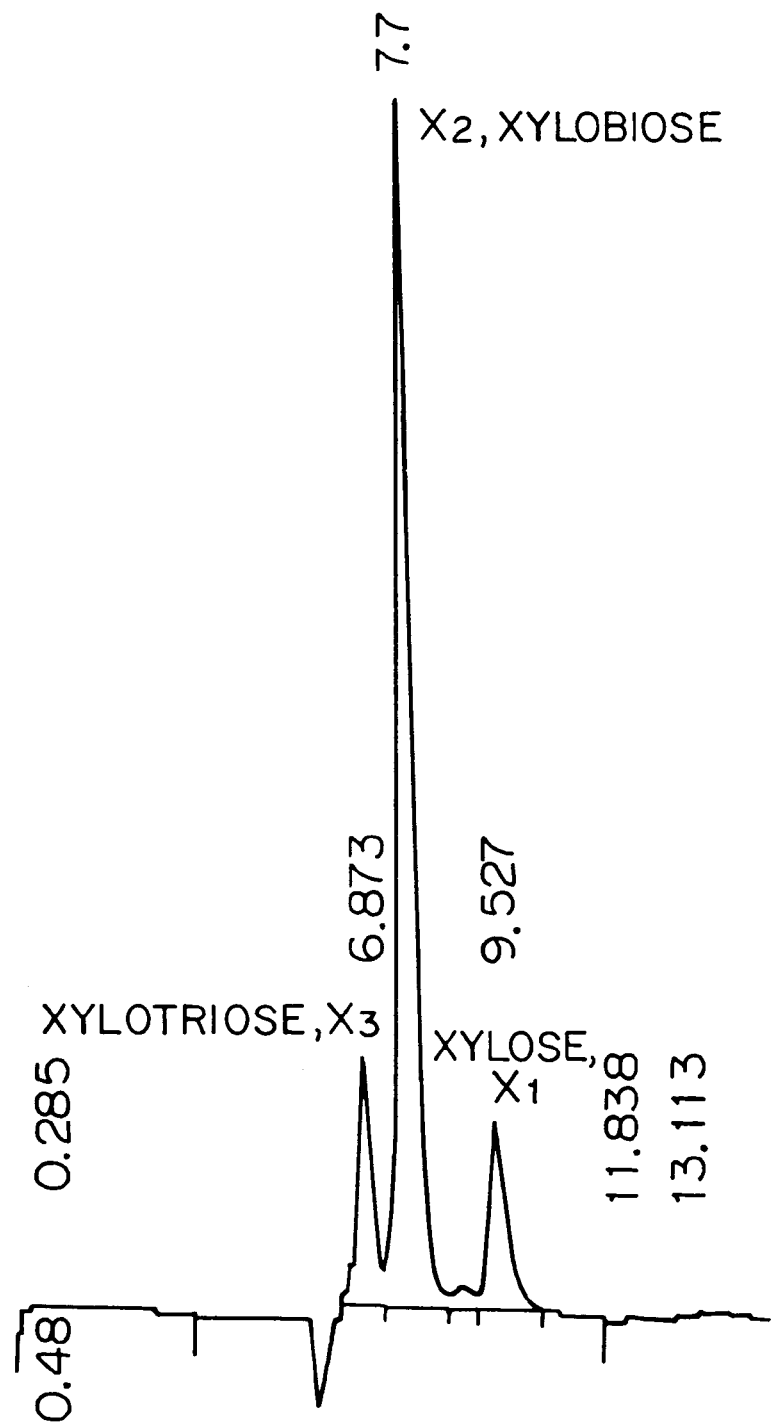
FIG. 1 shows the high-performance liquid chromatography (HPLC) of the xylooligosaccharide solution obtained in Example 1.

Xylooligosaccharide which is employed in the present invention is obtained by hydrolyzing or decomposing xylan. Xylan is one of the structurural polysaccharides which are widely distributed in nature, and it is made up of xylopyranose units connected by 1,4-β-linkages. Xylan resembles cellulose, but its molecular weight is relatively low, i.e., less than 30,000 (per 200 units of sugar). Sources of xylan are available widely in nature. Particularly suitable examples are corncob and cottonseed cake which have a high xylan content and malt cake and rice straw which are obtained in large amounts as industrial by-products.

Xylan is suitably hydrolyzed by enzymatic treatment or decomposed by physical treatment such as blasting treatment, or a combination of these treatments. In the case of enzymatic treatment, enzymes (xylanase) which are derived from microorganisms such as Asperillus (e.g., *Asperillus niger*) Trichoderma, Fusarium, Fumicola, etc. may be employed. By appropriately adjusting the temperature and pressure in a blasting process, it is possible to prepare various kinds of oligosaccharide. It is possible with either an enzymatic or blasting treatment to obtain an oligosaccharide with a polymerization degree varied to a certain extent. In particular, in the case of enzymatic treatment it is possible to obtain an oligosaccharide having a desired polymerization degree.

The xylooligosaccharide thus obtained basically consists of molecules of xylose which is a pentose sugar, the xylose molecules being connected by 1,4-β-linkages. In the case of xylobiose (polymerization degree 2; $X_2$), β-D-xylopyranosyl-(1→4)-D-xylopyranose is obtained; in the case of xylotriose (polymerization degree 3; $X_2$), β-D-xylopyranosyl-(1→4)-D-xylopyranosyl-(1→4)-D-xylopyranose is obtained. Samples which are obtained by decomposition of xylan have polymerization degrees within the range from 1 to 10. In the case of enzymatic treatment, it is particularly possible to obtain a xylooligosaccharide having a specific polymerization degree.

Xylooligosaccharide which is used as a *Bifidobacterium bifidum* proliferation promoting composition preferably contains a large amount of oligosaccharide which is not readily assimilated by *Escherichia coli* but is readily assimilated by *Bifidobacterium bifidum*. It is preferable in the present invention that xylooligosaccharide contains as its principal component xylobiose ($X_2$) which consists of two molecules of xylose connected by 1,4-β-linkages (the xylobiose content being preferably 60% or more). Although xylobiose alone may be used as a *Bifidobacterium bifidum* proliferation promoting substance, it is preferable from the viewpoint of industrial use to employ a xylooligosaccharide containing xylobiose as its principal component. Such a xylooligosaccharide can be obtained relatively easily by physically or enzymatically treating xylan or hemicellulose derived from a natural source, as has already been described and as will be described below through examples.

The xylooligosaccharide obtained as described above may be dissolved in water so as to be used as drinking water. The xylooligosaccharide may also be dissolved in juices or other beverages, or mixed with solid foods or with feed in the case where it is used for animals.

Xylooligosaccharide which is used as a *Lactobacillus bifidus* proliferation promoting composition may be employed in any form, i.e., in the form of either a liquid or powder in accordance with the use, but the xylooligosaccharide content is preferably from 1 to 10%.

The xylooligosaccharide that is employed in the present invention exhibits the advantage that it is more stable when exposed to acids and heat than other oligosaccharides as shown in the Examples which will be described later.

Assimilability of various saccharides with *Bifidobacterium bifidum* can be determined in such a manner that *Bifidobacterium longum* (hereinafter referred to as *B. longum*) or *Bifidobacterium adolescentis* (hereinafter referred to as *B. adolescentis*) is inoculated into each of the *Bifidobacterium bifidum* selecting media respectively having various saccharides added thereto, and changes in absorbance with the passage of time are measured, as described in detail in the following Examples. On the other hand, the *Bifidobacterium bifidum* proliferation promoting activity of oligosaccharides in vivo is measured by letting rats take in the form of drinking water an aqueous solution of an oligosaccharide to be examined, culturing a physiological saline suspension of the feces of each of the rats in an agar medium for selecting *Bifidobacterium bifidum*, and counting the number of colonies generated on the medium.

It has been found that xylooligosaccharide is assimilated by both *B. longum* and *B. adolescentis* and shows *Bifidobacterium bifidum* proliferation promoting activity in vivo also. It should be noted that *B. longum* which is employed in the present invention is available from ATCC (ATCC 15707).

The following Examples are provided for the purpose of further illustrating the present invention but are not to be construed as limiting.

EXAMPLE 1

Production of Xylooligosaccharide—Preparation from Hardwood Xylan by Enzymatic Process Eight kilograms of hardwood xylan (available from Sanyo-Kokusaku Pulp Co., Ltd) was suspended in 160 liters of water, and the pH of the resulting suspension was adjusted to 4.5 with HCl. Thereafter, 110 g (in terms of protein) of xylanase (available from Shin-Nihon Chemical Industry Co., Ltd.) derived from Trichoderma sp. was added to the suspension, and reaction was carried out for 2 hours at 55° C. After the completion of the reaction, 8 kg of powder active carbon was added to the reaction product, and the mixture was decolorized. Then, the active carbon having sugar adsorbed thereon was removed by a filter press and washed with 80 liters of 15% ethanol to collect sugar from the active carbon. Then, the collected sugar was treated with ion exchange resins (Amberlite IR-120B and Amberlite IRA410 available from Rohm & Haas Co., U.S.A.) to obtain a desalted saccharified product.

The sugar composition of xylooligosaccharide per solid content of the thus obtained saccharified product was analyzed by high-performance liquid chromatography (HPLC). The results showed that the xylooligosaccharide consisted of 23% of xylose, 64% of xylobiose, and 13% of xylotriose. The xylooligosaccharide solution was then purified by membrane concentration using a reverse osmosis membrane (available from Nitto Electric Industrial Co., Ltd.) to obtain a xylooligosaccharide solution consisting of 15% of xylose, 72% of xylobiose, and 13% of xylotriose, as shown by the HPLC pattern in FIG. 1. The thus obtained xylooligosaccharide solution was used for the following experiments carried out in vitro and in vivo.

Methods of producing xylooligosaccharide using materials or processes other than those described above will be explained through the following Examples.

EXAMPLE 2

Preparation of Xylooligosaccharide from Other Natural Materials by Enzymatic Process In this Example, xylooligosaccharide was prepared using corncob, cottonseed hull and malt cake as materials for xylan. One hundred grams (on a dry basis) of each of the above-mentioned xylan materials was dipped in 10 liters of a NaClO solution containing 2% of available chlorine for 15 hours at room temperature, and then washed with water and dried to obtain a deligninated material. The thus obtained material was dipped in a 24% KOH solution for 17 hours at 37° C., and then suction-filtered and washed with water to obtain a xylan extract. Further, the xylan extract was dialyzed by a cellulose membrane for 30 hours in running water. The dialyzed extract was then neutralized with 1N acetic acid and dried with ethanol, thereby obtaining xylan from each of the above-mentioned materials.

As an enzyme, 0.08 to 50 mg (in terms of protein) of xylanase (available from Shin-Nihon Chemical Industry Co., Ltd.) derived from Trichoderma sp. was added to 4 ml of an aqueous solution of the xylan obtained from each of the materials as described above, and reaction was carried out for 4 hours at 65 to 70° C. with pH adjusted at 5.3. As a result, a xylooligosaccharide solution containing 3 mg/ml of xylose and 16 mg/ml of xylobiose was obtained from xylan prepared from corncob, and a xylooligosaccharide solution containing 3 mg/ml of xylose and 15 mg/ml of xylobiose was obtained from xylan prepared from cottonseed hull. The xylooligosaccharide solution obtained from xylan prepared from malt cake contained 0.5 mg/ml of xylose and 7 mg/ml of xylobiose.

EXAMPLE 3

Preparation of Xylooligosaccharide by Other Processes (1) Preparation from malt cake by blasting process Thirty-five grams of dried malt cake was put in a blasting steaming apparatus (NAC-4 model, available from Nitto Autoclabe Co., Ltd.), and water was added thereto so that the water content was 7% (wt/v). Thereafter, the mixture was heated to 180° C. under stirring. After being maintained for 20 minutes in one case and for 0 minute in the other case at 180° C. and under 10 kg/cm$^2$G, the heated mixture was blown into an atmospheric pressure area. The thus processed sample was centrifuged for 10 minutes at 5,000 rpm to obtain a supernatant solution. It was confirmed from the results of HPLC analysis that the supernatant solution contained 55% of hemicelluloses having a polymerization degree of 5 or more in the case where the heated material was maintained for 20 minutes at 180° C. and under 180 kg/cm$^2$G, while 50% of such hemicelluloses was contained in the supernatant solution in the case where the maintenance time was 0 minute, and xylooligosaccharides such as xylose, xylobiose, xylotriose and xylotetraose were thus obtained.

(2) Preparation from malt cake by blasting extraction and enzymatic saccharification A solution containing 5% of hemicelluloses having a polymerization degree of 5 or more which were obtained in Example 3-(1) was charged in an immobilized enzyme carrier column formed by adsorbing 0.5 g (in terms of protein) of hemicellulase (available from Shin-Nihon Chemical Industry Co., Ltd.) derived from Trichoderma sp. on 5 g of cristobalite and cross-linking it with glutaraldehyde. Then, the solution was allowed to flow out at a flow rate of 2.5 ml/hr and at a temperature of 55° C., and the xylooligosaccharide content in the effluent was examined. The results showed that the xylose content was 4.5 g/l and the xylobiose content was 8.7 g/l.

EXPERIMENTAL EXAMPLE 1

Assimilability of Various Sugars with Enterobacteria

Assimilability of various sugars with enterobacteria were examined using as xylooligosaccharide the xylooligosaccharide solution obtained in Example 1 and as control sugars commercially available sugars. As enterobacteria, *Escherichia coli* (ATCC 25922) and *Bifidobacterium longum* (ATCC 15707) were employed. In the case of *E. coli*, 0.1 ml of a living bacterium suspension (10$^{13}$ cells/ml) was inoculated into 10 ml of culture media each containing 0.1% of one of the test sugars as a carbon source, and stationary culture was carried out at 37° C. Then, increases in the number of individuals of each of the bacteria were obtained by measuring changes in absorbance at 660 nm with the passage of time to thereby examine the assimilability of each of the test sugars. In the case of *B. longum*, 0.1 ml of a living bacterium suspension (10$^{15}$ cells/ml) was inoculated into 10 ml of culture media each containing 1.1% of skimmilk powder and 0.2% of one of the test sugars as a carbon source, and each of the bacteria was thereby cultured under anaerobic conditions at 37° C. Then, increases in the number of individuals of each of the bacteria were obtained by measuring changes in absorbance at 660 nm with the passage of time to thereby examine the assimilability of each of the test sugars. As the culture media for examining assimilability, Gray & Tatum media were employed for *E. coli*, while ordinary media for *Bifidobacterium bifidum* were employed for *B. longum*.

FIG. 2-A shows proliferation profiles of *E. coli*, and FIG. 2-B shows proliferation profiles of *B. longum*. The results of the experiments have confirmed that the xylooligosaccharide according to the present invention is assimilated by *B. longum* in the same manner as in the other saccharides which are considered to be assimilable with *B. longum*. On the other hand, the xylooligosaccharide of the present invention is not readily assimilated by *E. coli* in comparison with lactose, lactulose and xylose although it is readily assimilated by *E. coli* in comparison with fructooligosaccharide. Thus, it has been confirmed that the xylooligosaccharide may be employed as an agent which is capable of selectively promoting proliferation of *Bifidobacterium bifidum*.

Further, the assimilability of various saccharides was also examined in regard to *E. coli* (NCTC 9001) preserved at National Collection of Type Culture (NCTC: London) and *B. adolescentis* which is another kind of *Bifidobacterium bifidum*. Experiments were carried out in the same manner as in Experimental Example 1 except that the concentration of each saccharide was doubled (i.e., 0.2% in the case of *E. coli*; 0.4% in the case of *B. adolescentis*). The results of the experiments are shown in FIGS. 5-A (*E. coli*) and 5-B (*B. adolescentis*).

In the case of *E. coli* (NCTC 9001), no significant difference is to be found between the oligosaccharides in terms of assimilability except for straight chain oligosaccharide, whereas, in the case of *Bifidobacterium bifidum* (*B. adolescentis*), xylooligosaccharide shows clearly superior assimilability to those of the other oligosaccharides in the same way as in the case of *Bifidobacterium bifidum* (*B. longum*) shown in FIG. 2-B, and this shows that the composition according to the present invention is suitable for proliferation of *Bifidobacterium bifidum*.

It should be noted that the xylooligosaccharide solutions obtained by the other preparation methods (Examples 2 and 3) also had *Bifidobacterium bifidum* proliferation promoting activity similar to the above, although no data is shown herein.

EXPERIMENTAL EXAMPLE 2

Stability of Xylooligosaccharide

The xylooligosaccharide obtained in Example 1 and a commercially available fructooligosaccharide were compared with each other in terms of stability in a solution state as follows.

Xylooligosaccharide and fructooligosaccharide were each dissolved in each of the four solvents, i.e., McIlvaine buffers with pH values 3, 5 and 8, respectively, and $H_2O$, to prepare a solution having a saccharide concentration of 10%.

Each of the saccharide solutions was maintained in boiling water of 100° C. for 30 minutes in one case and for 60 minutes in the other case. Thereafter, the sugar composition of each of the solutions was measured by HPLC, and the residual rates of xylooligosaccharide and fructooligosaccharide were obtained respectively by making a comparison between the contents of xylooligosaccharide (including $X_2$ and $X_3$) and fructooligosaccharide (including $GF_2$, $GF_3$ and $GF_4$) before and after the maintaining period.

It should be noted that the residual rates are shown as follows:

In the case of xylooligosaccharide, $$\frac{(X_2 + X_3)\text{sample}}{(X_2 + X_3)\text{contol}} \times 100(\%)$$

In the case of fructooligosaccharide, $$\frac{(GF_2 + GF_3 + GF_4)\text{sample}}{(GF_2 + GF_3 + GF_4)\text{control}} \times 100(\%)$$

The results of examination of each of the oligosaccharides are shown in Table 1. In Table 1 and the above-described formulae, $X_1$, $X_2$ and $X_3$ represent xylose, xylobiose and xylotriose, respectively, and GF2, GF3 and GF4 represent fructooligosaccharides consisting of one molecule of glucose (glu) and two, three or four molecules of fructose (fru), respectively. "Suc" denotes sucrose.

of the present invention may be added to various kinds of fruit juice beverages of low pH and employed as *Bifidobacterium bifidum* proliferation promoting beverages.

EXPERIMENTAL EXAMPLE 3

*Bifidobacterium bifidum* Proliferation Activity in vivo of Xylooligosaccharide

The xylooligosaccharide obtained in Example 1 and a commercially available fructooligosaccharide were compared with each other to examine the entero *Bifidobacterium bifidum* proliferation activity by using rats.

Experiments were carried out on a xylooligosaccharide intake group of rats and a fructooligosaccharide intake group of rats, each group consisting of three 108-day old rats. Each oligosaccharide was prepared in the form of a 3% aqueous solution. Each rat was given water for the first two days, the above-described aqueous oligosaccharide solution for the following three days, and water for the following two days, the water and solution being fed as drinking water. One gram of feces of each rat was collected at three different times, i.e., during the first two days (before the intake of oligosaccharide), on the fifth day (on the third day after the start of intake of oligosaccharide), and on the seventh day (on the second day after the stop of intake of oligosaccharide), and the collected bulk of feces was suspended in 9 ml of anaerobic sterilized saline using a sterilized Teflon homogenizer in the CO2 gas atmosphere under

TABLE 1

Stability of Oligosaccharides

| | | Xylooligosaccharide | | | | Fructooligosaccharide | | | | | | |
|---|---|---|---|---|---|---|---|---|---|---|---|---|
| Treatment | | | | | Residual | | | | | | | Residual |
| | Treating | Composition (%) | | | rate | Composition (%) | | | | | | rate |
| pH | time | $X_1$ | $X_2$ | $X_3$ | (%) | fru | glu | Suc | $GF_2$ | $GF_3$ | $GF_4$ | (%) |
| Controls (untreated) | | 13.0 | 71.0 | 16.0 | 100 | 1.2 | 1.3 | 4.0 | 32.6 | 49.3 | 11.6 | 100 |
| 3 | 30 (min) | 13.6 | 71.6 | 14.8 | 98.2 | 48.7 | 18.0 | 30.1 | 0.7 | 1.8 | 0.7 | 3.4 |
| | 60 | 14.2 | 71.0 | 14.8 | 97.5 | 57.4 | 28.2 | 14.3 | <0.5 | <0.5 | <0.5 | <2 |
| 5 | 30 | 12.3 | 70.7 | 16.0 | 98.5 | 2.5 | 1.8 | 6.0 | 31.5 | 46.6 | 11.6 | 95.9 |
| | 60 | 12.4 | 71.2 | 15.2 | 98.2 | 3.7 | 2.0 | 7.4 | 31.1 | 44.5 | 11.3 | 92.9 |
| 8 | 30 | 14.7 | 66.7 | 13.6 | 91.3 | 1.2 | 1.3 | 4.1 | 32.6 | 49.2 | 11.6 | 99.9 |
| | 60 | 16.0 | 65.8 | 13.6 | 90.2 | 0.7 | 1.1 | 4.3 | 32.6 | 49.4 | 11.6 | 100 |
| 7 ($H_2O$) | 30 | 13.1 | 71.4 | 15.6 | 98.9 | 1.7 | 1.2 | 4.8 | 32.3 | 48.4 | 11.6 | 98.7 |
| | 60 | 13.1 | 71.7 | 15.0 | 98.8 | 2.2 | 1.4 | 5.5 | 32.5 | 47.2 | 11.2 | 97.2 |

As will be understood from Table 1, the stability of fructooligosaccharide in the acidic region is considerably inferior, whereas xylooligosaccharide is stable over a wide range of pH region including the acidic region. The high-stability characteristics of xylooligosaccharide show that it is stably maintained even in the gastric juice having a relatively low pH value. The above-described experimental results, together with the results of experiments in vivo described below, show that the xylooligosaccharide composition according to the present invention is superior to the conventional oligosaccharide as being a *Bifidobacterium bifidum* proliferation promoting agent. The above-described experimental results also show that the xylooligosaccharide ice cooling. Then, the suspension was appropriately diluted with anaerobic sterilized saline under anaerobic conditions, and 0.1 ml of the dilute solution was plated on a *Bifidobacterium bifidum* selecting (BS) agar medium. After anaerobic culture had been carried out for 3 days at 37° C., the number of colonies of Bifidobacterium generated on the medium was counted to obtain a change in the number of individuals of entero *Bifidobacterium bifidum*. Further, the weight, water intake and diet intake of each rat were measured every day. Table 2 shows changes in the number of entero *Bifidobacterium bifidum* in 1 g of feces of each rat, and Table 3 shows averaged numbers (represented by logarithmic values) of individuals of entero *Bifidobacterium bifidum* for the two groups of rats.

TABLE 2

Changes in number of entero Bifidobacterium bifidus in rats

| | Bifidobacterium (number/gram of feces) | | | | | |
|---|---|---|---|---|---|---|
| | Before intake | | On the third day after intake started | | On the second day after intake ceased | |
| Samples | | logarithmic value | | logarithmic value | | logarithmic value |
| Fructooligosaccharide | $4.8 \times 10^6$ | 6.7 | $3.5 \times 10^6$ | 6.5 | $6.5 \times 10^6$ | 6.8 |
| | $5.9 \times 10^5$ | 5.8 | $1.9 \times 10^7$ | 7.3 | $1.3 \times 10^7$ | 7.1 |
| | $3.3 \times 10^6$ | 6.5 | $4.1 \times 10^6$ | 6.6 | $5.7 \times 10^6$ | 6.8 |
| Xylooligosaccharide | $4.9 \times 10^5$ | 5.7 | $2.6 \times 10^6$ | 6.4 | $6.5 \times 10^6$ | 6.8 |
| | $1.4 \times 10^6$ | 6.1 | $1.5 \times 10^6$ | 6.2 | $6.1 \times 10^6$ | 6.8 |
| | $4.2 \times 10^5$ | 5.6 | $3.0 \times 10^7$ | 7.5 | $8.9 \times 10^6$ | 6.9 |

TABLE 3

Averaged logarithmic value for each group (average ± S.D.)

| Samples | Before intake | On the third day after intake started | On the second day after intake ceased |
|---|---|---|---|
| Fructooligo-saccharide | 6.3 ± 0.4 | 6.8 ± 0.4 | 6.9 ± 0.1 |
| Xylooligosaccharide | 5.8 ± 0.2 | 6.7 ± 0.6 | 6.8 ± 0.0 |

FIG. 3 shows changes in the number of individuals of entero *Bifidobacterium bifidum* in a group of rats to which xylooligosaccharide was administered and in a group of rats to which fructooligosaccharide was administered.

It will be understood from Table 2 and FIG. 3 that there is a significant difference in terms of the *Bifidobacterium bifidum* proliferation promoting activity between a group of rats to which xylooligosaccharide was administered and a group of rats to which no xylooligosaccharide was administered, although there are variations among individuals. This effect is by no means inferior to that of fructooligosaccharide, and the above-described experimental results, in conjunction with the aforementioned data concerning stability, show that the xylooligosaccharide of the present invention is remarkably useful as a *Bifidobacterium bifidum* proliferation promoting agent.

FIG. 4 shows changes in the weight, diet intake and water intake of a group of rats to which xylooligosaccharide was administered and a group of rats to which fructooligosaccharide was administered. Although there are variations in the water intake (including samples taken in during the period from the third day to the fifth day), no substantial change is found in terms of either the weight or the diet intake. Since rats that had relatively high levels of water intake exhibited a particularly high increase in the number of individuals of entero *Bifidobacterium bifidum* (see FIG. 3), it may be considered that the increase in the number of individuals of entero *Bifidobacterium bifidum* is attributed to the effects of these oligosaccharides (it should be noted that the marks ○(A), Δ(B) and x (C) in the figures correspond to the respective rats).

What is claimed is:

1. A method for promoting proliferation of *Bifidobacterium Bifidum* by administering to a human, a mixture of xylooligosaccharides in an amount effective for promoting proliferation of *Bifidobacterium Bifidum* in the intestine, said mixture of xylooligosaccharides comprising xylobiose as its principal component.

2. The method according to claim 1, wherein said xylooligosaccharides are obtained by enzymatically or physicochemically treating either xylan or hemicellulose derived from a natural source.

3. The method according to claim 1 which is non-toxic to animals including man.

4. A method of claim 1 wherein said mixture of xylooligosaccharides contains more than 70% of xylooligosaccharides.

5. A method according to claim 1 wherein the xylobiose content in said mixture of xylooligosaccharides is more than 50%.

6. A method according to claim 5 wherein the xylobiose content is more than 60%.

* * * * *